United States Patent
Grichko et al.

(10) Patent No.: US 8,323,976 B2
(45) Date of Patent: Dec. 4, 2012

(54) ALTERATIONS UTILIZING NANOPARTICLES

(75) Inventors: Varvara Grichko, Raleigh, NC (US); Olga Alexander Shenderova, Raleigh, NC (US)

(73) Assignee: International Technology Center, Raleigh, NC (US)

( * ) Notice: Subject to any disclaimer, the term of this patent is extended or adjusted under 35 U.S.C. 154(b) by 1255 days.

(21) Appl. No.: 11/795,292

(22) PCT Filed: Jan. 18, 2006

(86) PCT No.: PCT/US2006/001572
§ 371 (c)(1),
(2), (4) Date: Jan. 29, 2008

(87) PCT Pub. No.: WO2006/078640
PCT Pub. Date: Jul. 27, 2006

(65) Prior Publication Data
US 2008/0194031 A1 Aug. 14, 2008

Related U.S. Application Data

(60) Provisional application No. 60/645,408, filed on Jan. 19, 2005.

(51) Int. Cl.
*C12N 15/87* (2006.01)
*C12N 5/10* (2006.01)
(52) U.S. Cl. .......... 435/459; 435/470; 435/325
(58) Field of Classification Search ........... 435/459, 435/470, 325
See application file for complete search history.

(56) References Cited

U.S. PATENT DOCUMENTS

| 6,165,440 A * | 12/2000 | Esenaliev ............ 424/1.11 |
| 6,475,994 B2 * | 11/2002 | Tomalia et al. ........ 514/44 R |
| 2004/0076681 A1 | 4/2004 | Dennis et al. |
| 2005/0277160 A1 | 12/2005 | Shiba et al. |

FOREIGN PATENT DOCUMENTS

WO  WO 2004-089818 A1  10/2004

OTHER PUBLICATIONS

Huang and Chang (2004) Langmuir, vol. 20 (14), 5879-5884.*
Notification Concerning Transmittal of International Preliminary Report on Patentability (Form PCT/IB/326); International Application No. PCT/US2006/001572; Filing Date: Jan. 18, 2006.
R. Kumar et al., "Nanoparticle-mediated gene delivery: state of the art", 2004, Ashley Publications Ltd, ISSN 1471-2598.
International Search Report; Application No. PCT/US06/01572; Filing Date: Jan. 18, 2006.
Written Opinion of the International Searching Authority; Application No. PCT/US06/01572; Filing Date: Jan. 18, 2006.

* cited by examiner

*Primary Examiner* — Anne Marie S Wehbe
(74) *Attorney, Agent, or Firm* — Rader, Fishman & Grauer PLLC

(57) ABSTRACT

Alterations utilizing nanoparticles. Certain embodiments of the invention are methods of delivering a substance to a target using a delivery-aid which includes nanoparticles. Those nanoparticles may be nanocarbon particles. Other embodiments are methods of delivering nanoparticles to a target involving placing a mask between a source of ballistic delivery of nanoparticles and the target. Other embodiments include irradiating a target to cause localized heating of the region of the target in which the nanodiamonds or OLC particles are present. Other embodiments utilize nanoparticles to make cells competent for genetic transformation. This abstract is not to be considered limiting, since other embodiments may deviate from the features described in this abstract.

18 Claims, 15 Drawing Sheets

ALTERATIONS UTILIZING NANOPARTICLES

CROSS-REFERENCE TO RELATED APPLICATIONS

This application claims priority from U.S. Provisional Application No. 60/645,408 filed on 19 Jan. 2005 entitled "DELIVERY OF BIO-AGENTS", which is incorporated by reference herein.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT REFERENCE TO SEQUENCE LISTING, A TABLE, OR A COMPUTER PROGRAM LISTING COMPACT DISK APPENDIX

Not applicable

BACKGROUND

Diverse methods have been previously disclosed for transferring materials into cells. The materials being transferred may be, for example, nucleic acid molecules, stains, or chemicals which influence the physiology of the target cell. These methods include biolistic methods. Typically, in biolistics, tungsten or gold particles are coated with the substance to be introduced into the cell and are caused to contact the cell at high velocity. Although various biolistic and biolistic-like methods have been developed, including those that use particles other than tungsten and gold, none has proven totally satisfactory for all purposes.

As used in this application, the term "biologically active substance" means a substance or its precursor or a mixture of thereof that can influence the physiology of a target cell, organism or structure including metabolically active cells. Examples of structures including metabolically active cells include, without limitation, fruit removed from the plant and surgically removed animal organs.

The efficiency of genetic transformation varies widely between organisms and within a given organism based on environmental treatment. Diverse methods have been used to increase the transformation efficiency of organisms. Organisms which have been rendered receptive to genetic transformation are commonly referred to as "competent cells." There is no agreed upon standard as to the efficiency of transformation which causes a cell to be considered "competent." No method for making cells competent has proven suitable for all circumstances.

Nanodiamond (ND) particles consist of cubic (or hexagonal) diamond phase in the core of the particles and different functional groups on the particle surface. Reported methods of ND particle synthesis are very diverse. Examples of ND synthesis methods include a gas phase nucleation at ambient pressure, chlorination of carbide material at moderate temperatures, high pressure-high temperature graphite transformation within a shock wave, or carbon condensation during detonation of carbon-containing explosives. However, the "nanodiamond" and "ND" as used in this disclosure embraces particles produced in other manners including manufacturing methods not yet discovered. The term nanodiamond also embraces agglomerates of primary nanodiamond particles. Agglomerate sizes, in principle, can be up to several microns.

For purposes of this document, the term onion-like carbon (OLC) particles is used to refer to nanoparticles such as those disclosed by Kuznetsov et al. (in Russian Patent document 2094370, which is hereby incorporated by reference) which are characterized as layered carbon structures. Such OLC particles are not to be confused with carbon onions. While carbon onions are structures made up of enclosed fullerenes, OLC particles are nano-particles of a different class made up of concentric carbon shells which have one or more defects in one or more of the carbon shells. Several different types of defects have been noted including (holes, unpaired electrons, $sp^2/sp^3$ irregularities, etc.). OLC shells can be rounded or elongated and several smaller OLC particles can form agglomerates where the whole agglomerate is sometimes enclosed in a larger graphite-like shell. The term OLC will also be used to refer to such agglomerations of OLC particles. OLC particles have been obtained by annealing of nanodiamonds, but use of this term should not preclude other manufacturing methods including manufacturing methods as yet undiscovered.

Depending on the annealing temperature, OLC particles have one or more structural defects. In OLC particles there can be a combination of $sp^2/sp^3$ types of bonding while ideal carbon onions are made of $sp^2$ type shells. Ideal carbon onions are made up of layers of enclosed fullerene molecules of differing sizes (e.g., C60, C240, C540, C960, etc.). An OLC is therefore not, strictly speaking, a caged compound. Usually, but not always, the term "OLC particles" is used in connection with particles having a substantial number of structural defects, however, a single defect may be sufficient to distinguish between carbon onions and OLC particles. The term OLC also embraces agglomerates of OLC particles. When annealing temperature is below approximately 1400-1800K, hybrid structures composed of diamond core surrounded by onion-like carbon shells can be obtained. The term OLC also embraces these hybrid structures.

Carbon nanotubes and carbon nanohorns are each examples of nanostructures which are at least principally composed of carbon in a graphite-like configuration. Nanohorns have a horn-like particle shape. Production of nanohorns has included laser ablation of graphite. However, the term "nanohorn" is taken here to include the same or similar nanostructures made by other manufacturing methods, including manufacturing methods as yet undiscovered. Nanotubes are generally cylindrical in shape. There are multi-walled and single walled nanotubes. Multi-walled nanotubes can be made by standard arc-evaporation. Single walled nanotubes can be made, for example, by addition of metals (e.g., cobalt) to the graphite electrodes or by laser-vaporization of graphite. However, the term "nanotube" is taken here to include the same or similar nanostructures made by other manufacturing methods including manufacturing methods as yet undiscovered.

In this disclosure, the term "nanocarbon" refers to OLC, carbon onions, ND, carbon nanotubes, carbon nanohorns, diamondoids and all other nanoparticles which are composed principally of carbon.

As used in this disclosure, cells of a specified category of living thing includes, without limitation, in vivo cells, cells in culture and cells removed from the whole organism. By way of example, the term "insect cells" would embrace cells in whole insects, cultured cells of cell lines derived from insects, and cells removed from whole insects.

Figure 1:
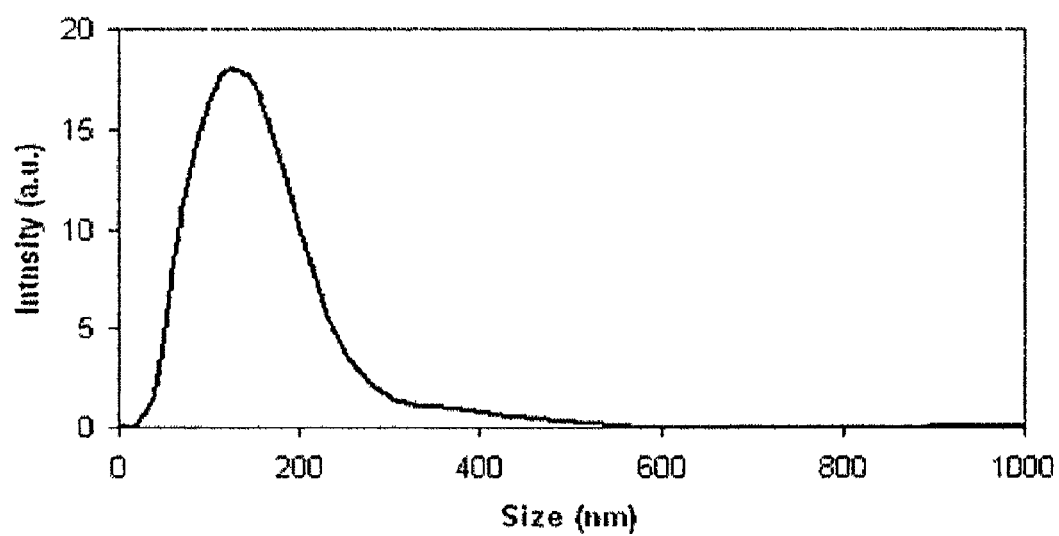
FIG. 1 is a presentation of the size distribution information for a particular batch of ND particles.

DETAILED DESCRIPTION OF SPECIFIC EMBODIMENTS OF THE INVENTION:

The invention disclosed in certain exemplary embodiments here relates, in brief, to the delivery of a material to another material using a high carbon content delivery particle. This includes, but is not limited to, biolistic delivery of materials into cells, tissue, fluids or organs of living organisms. It also includes, but is not limited to, delivery of materials into non-living materials. It also includes delivery of materials into materials (living or non-living) without employment of high velocity contact between the particle and the target. Other variations are disclosed below.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

EXAMPLE I

Except as specified, all steps were at room temperature.

The lux plasmid DNA was purchased from Modem Biology, Inc. (West Lafayette, Ind.). The plasmid has been constructed by cloning lux operon from *Vibrio fischeri* into the pUC18 plasmid. Bacteria transformed with the lux plasmid both glow in the dark and are resistant to ampicillin. The lux plasmid was amplified in *Eshcerichia coli* DH5 (ATCC 53868; Genotype: F-, supE44, hsdR17, recA1, gyrA96, endA1, thi-1, relA1, deoR, lambda-) and isolated by conventional methods.

Detonation ND particles were purchased from a commercial vendor. FIG. 1. is a graph of size distribution of typical ND particles used in the examples dispersed in water solvent measured using the photon correlation spectroscopy approach (Beckman Coulter N5 particle size analyzer). The particle size determined using the dynamic light scattering method is an average value, weighted by the particle scattering intensity. A water suspension of approximately 500 mg of the commercially acquired material was put through a 1 inch diameter, 0.45 µm nominal pore size Millipore nylon filter. The ND particles were repeatedly washed in distilled water through cycles of suspension and centrifugation. The particle suspension was sterilized by autoclaving. A stock suspension of the ND particles in 500 µL of water was stored at approximately 4° C. until use.

On a day of bombardment, 5 µL of 1 µg/µL lux plasmid DNA dissolved in Tris-EDTA buffer (0.5 mM EDTA, 10 mM Tris-HCl, pH 8.0), 50 µL of 2.5 M calcium chloride and 20 µL of freshly prepared 0.1 M spermidine was added to the 50 µL ND stock suspension while continuously vortexing. The suspension was mixed by vortexing at 600 rpm for 10 min. After being kept on ice for 5-10 min, the plasmid-ND particles were harvested by centrifugation and resuspended in absolute ethanol. The plasmid-ND particles were then harvested again and resuspended in 60 µL of fresh absolute ethanol. A 10 µL sample of the plasmid-ND-ethanol suspension was pipetted onto the center of a Bio-Rad 11-inch macrocarrier disk in one quick motion, and the macrocarrier was left to air-dry.

The bacteria were grown with agitation at 37° C. overnight in 15 ml of nutrient broth. Cells were harvested by centrifugation and resuspended in 1 ml of nutrient broth.

A Bio-Rad 1-inch macrocarrier separating paper disk was sterilized by soaking in ethanol, air-dried, then placed on nutrient agar in a 3.5-inch sterile polystyrene Petri dish. After allowing the separating paper disk to absorb moisture, 100 µL of resuspended bacteria were pipetted onto the disk. Ballistic delivery was accomplished using a Bio-Rad PDS-1000/He system. The macrocarrier launch assembly was positioned in the slot closest to the top of the chamber so that the 1,100 psi rupture disk was just above the lid of the macrocarrier launch assembly. The gap distance between the macrocarrier and the sample was about 2 inches. Bombardment was performed when the chamber pressure was reduced to 25 mm Hg, and the He pressure was 1,100 psi. After the bombardment, bacteria were given time to recover. Then the paper disk was transferred to a sterile tube filled with 5 ml of nutrient broth with 100 µg/ml ampicillin and the contents were vortexed in order to fully separate cells from the disk. The disk was then carefully removed, and cells were collected by centrifugation. The cells were resuspended in 0.5 ml of nutrient broth and 100 µL were plated on each of five plates of nutrient agar with 100 µg/ml ampicillin. Bioluminescence of 12 colonies on the plates was observed on the third day of growth. No bioluminescent colonies were observed on the control plates which contained bacteria bombarded with ND particles without plasmid or plates which contained bacteria mixed with plasmid and exposed to a He blast.

EXAMPLE II

This example is essentially the same as Example I, except that pUC18 was used instead of the lux plasmid, plating was onto LB agar with 100 µg/ml ampicillin, and incubation of plates was at room temperature. The pUC18 DNA was purchased from Modern Biology, Inc. (West Lafayette, Ind.). Plasmid pUC18 contains 2,686 nucleotide pairs. Plasmid pUC18 codes for β-galactosidase and β-lactamase. Twenty-one white colonies were observed on the third day of growth. No colonies were observed on the control plates which contained bacteria bombarded with ND particles without plasmid or plates which contained bacteria mixed with plasmid and exposed to a He blast.

EXAMPLE III

This example is essentially the same as Example II except that $E.$ $coli$ DH5α (Genotype: F-, ϕ80dlacZΔM15, Δ(lac-ZYA-argF)U169, deoR, recA1, endA1, hsdR17(rk–, mk+), phoA, supE44, λ-, thi-1, gyrA96, relA1) (Life Technologies, Inc) was used instead of ATCC 53868, plating was onto LB agar containing 150 µg/ml ampicillin, 0.1 mM IPTG and 60 µg/ml X-gal (Teknova Inc., Hollister, Calif.). Nine blue colonies were observed on the second day of growth. No blue colonies were observed on the control plates which contained bacteria bombarded with ND without plasmid or plates which contained bacteria mixed with plasmid and exposed to a He blast. For this experiment, each blue colony was presumptively founded from a genetically transformed cell.

EXAMPLE IV

Figure 2:
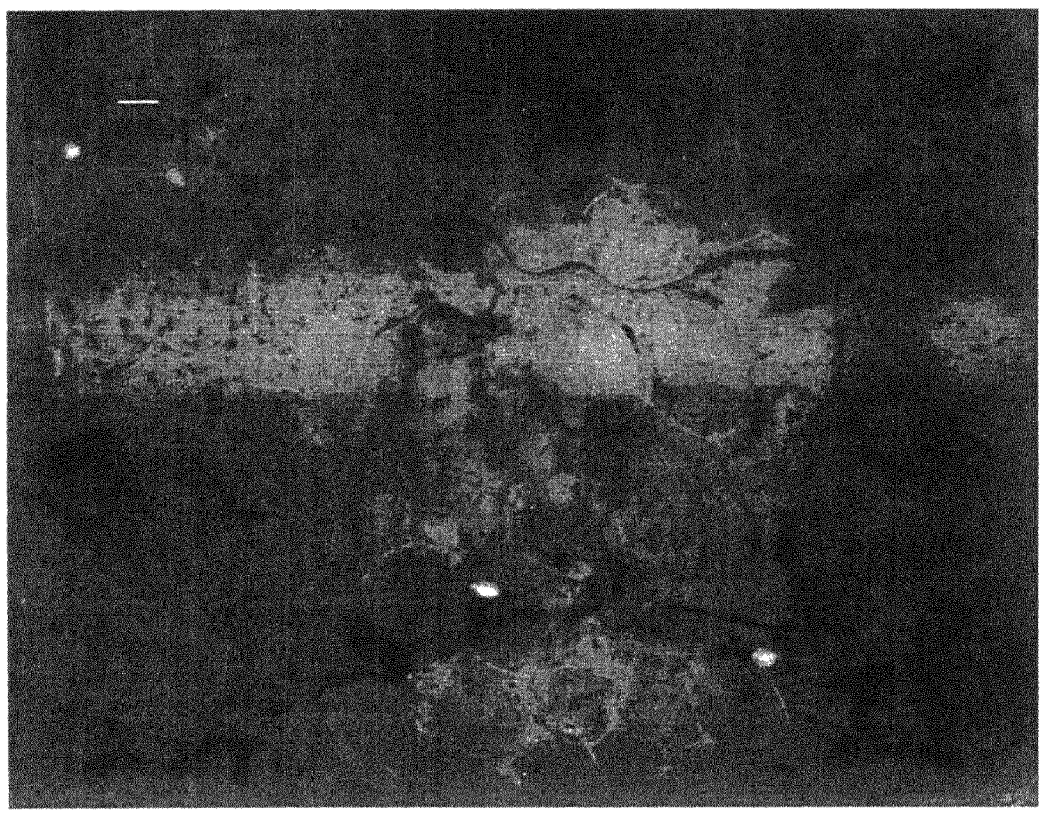
FIG. 2 is a micrograph of the results described in Example IV.

ND particles from the same stock suspension as used in Example I were surface-oxidized and aminated. They were then labeled using the Alexa Fluor 350 (Molecular Probes, Eugene, Oreg.). Those labeled ND particles were delivered to banana fruit peel using the Bio-Rad PDS-1000/He system with an 1100 psi rupture disk. The presence of fluorescent particles was confirmed using an Olympus IX71 inverted fluorescence microscope. A micrograph of typical results is shown as FIG. 2. In that micrograph, the scale bar is 50 µm.

EXAMPLE V

Figure 3:
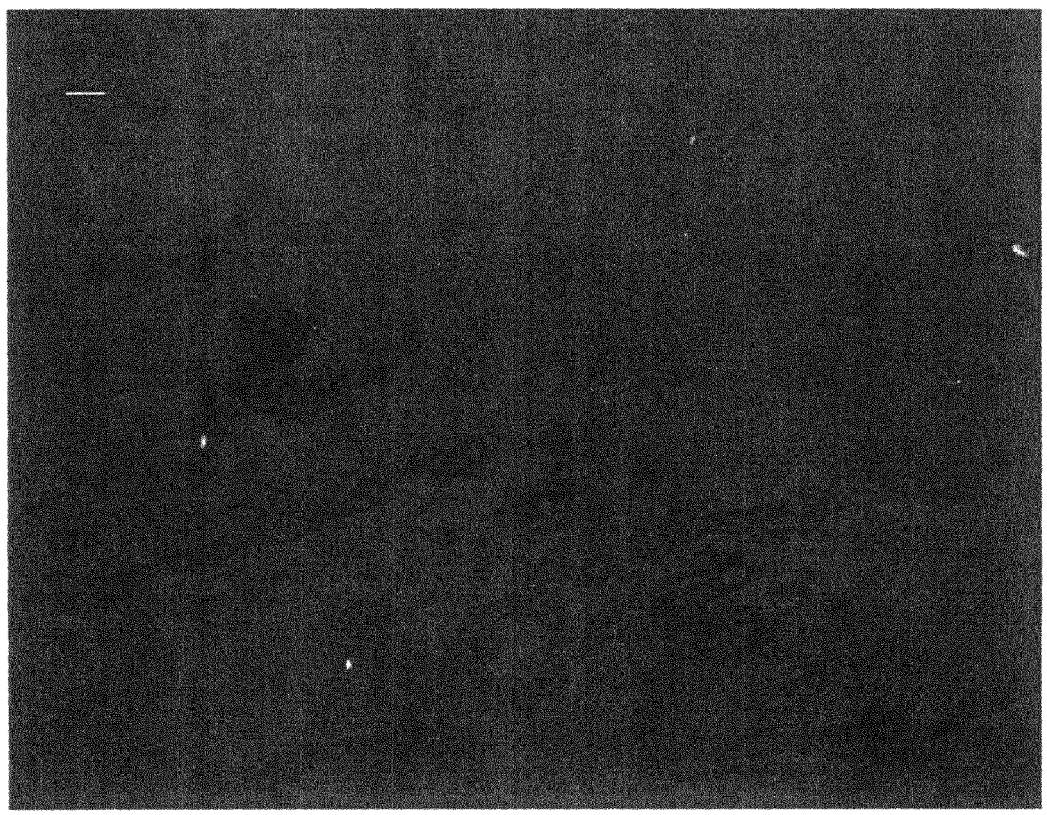
FIG. 3 is a micrograph of the results described in Example V.

This example is essentially the same as Example IV, except that banana fruit pulp was substituted for the banana fruit peel. The presence of fluorescent particles was confirmed using an Olympus IX71 inverted fluorescence microscope. A micrograph of typical results is shown as FIG. 3. In that micrograph, the scale bar is 50 µm.

EXAMPLE VI

Figure 4:
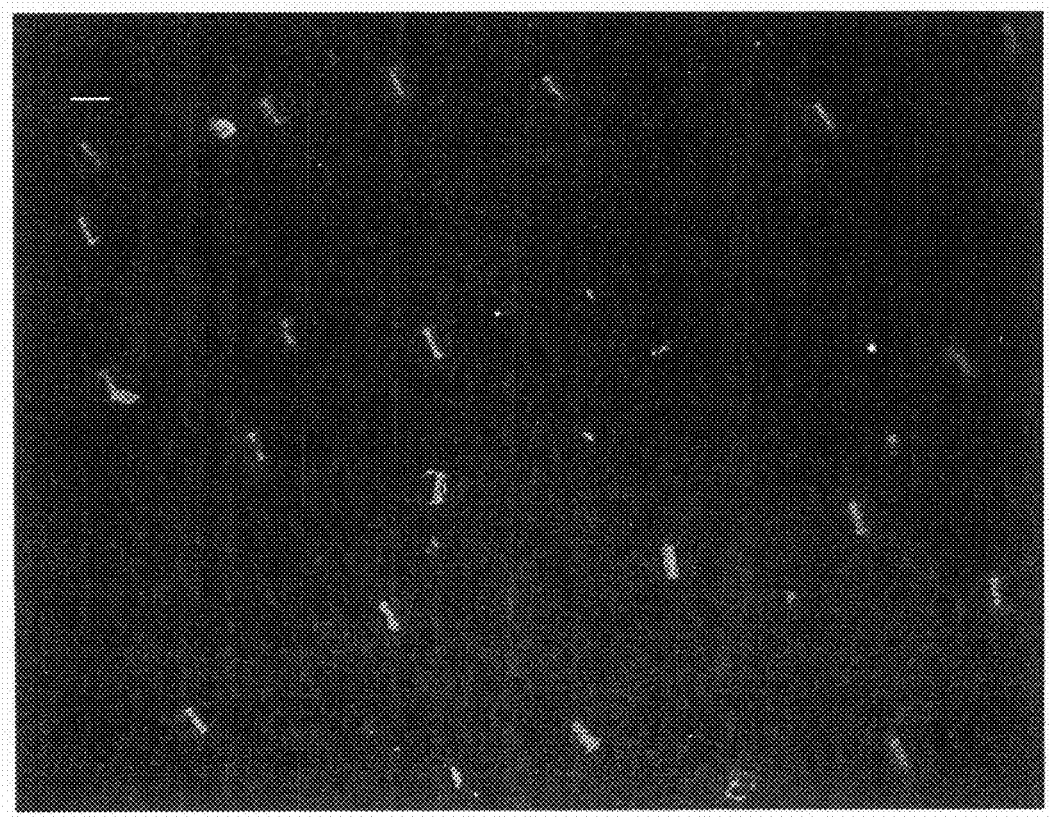
FIG. 4 is a micrograph of the results described in Example VI.

This example is essentially the same as Example IV, except that a detached green flattened stem of zygocactus (*Schlumbergera bridgesii* var. Magenta) was substituted for the banana fruit peel. The presence of fluorescent particles was observed using an Olympus IX71 inverted fluorescence microscope. A micrograph of typical results is shown as FIG. 4. In that micrograph, the scale bar is 50 µm.

EXAMPLE VII

ND particles from the same stock suspension as used in Example I were coated with 4.3-kb pFL445 yeast vector DNA (ATCC number 77205) by a method essentially as in Example I. Ballistic delivery to *Saccharomyces cerevisiae* ura3-52 mutant (ATCC number 204152) was accomplished using a Bio-Rad PDS-1000/He system. pFL445 carries ampR and URA3 genes and thus allows complementation. Yeast cells were spread onto the center of a Petri dish and immediately bombarded. After the bombardment, yeast were kept in regeneration medium for 1 h and 100 µL were plated on each of five selective plates without uracil (Teknova, Hollister, Calif.). A total of 104 colonies appeared on the plates. No colonies were observed on the control plates which contained yeast mixed with DNA plasmid and exposed to the helium gas blast.

EXAMPLE VIII

This example is essentially the same as Example IV, except that suspension culture of fall armyworm (*Spodoptera frugiperda*, Sf9, ATCC CRL-1711) was substituted for the banana fruit peel. The presence of fluorescent particles was observed using an Olympus IX71 inverted fluorescence microscope.

EXAMPLE IX

Figure 6:
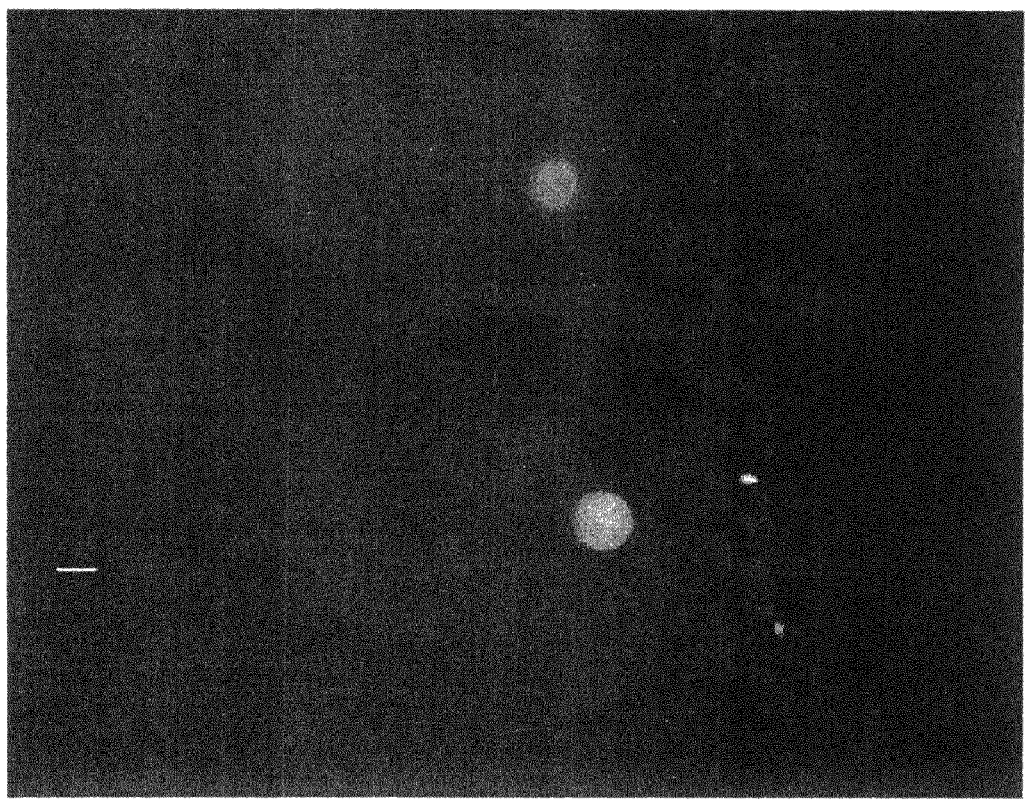
FIG. 6 is a micrograph of the results described in Example IX.

This example is essentially the same as Example IV, except that detached human finger nail was substituted for the banana fruit peel. The presence of fluorescent particles inside the target was observed using an Olympus IX71 inverted fluorescence microscope. A micrograph of typical results is shown as FIG. 6. In that micrograph, the scale bar is approximately 50 µm.

EXAMPLE X

ND particles from the same stock suspension as used in Example I were mixed with cresol red and air-dried. Those ND particles were delivered to polystyrene foam using the Bio-Rad PDS-1000/He system with an 1100 psi rupture disk. After cleaning with air blasts and slicing the sample, it was observed that color was imparted to the polystyrene foam.

EXAMPLE XI

ND particles from the same stock suspension as used in Example I were surface-oxidized and attached to poly-L-lysine-FITC. Those labeled ND particles were delivered to a United States one dollar bill using the Bio-Rad PDS-1000/He system with an 1100 psi rupture disk. The presence of fluorescent particles inside the bill was observed using an Olympus IX71 inverted fluorescence microscope.

EXAMPLE XII

Figure 7:
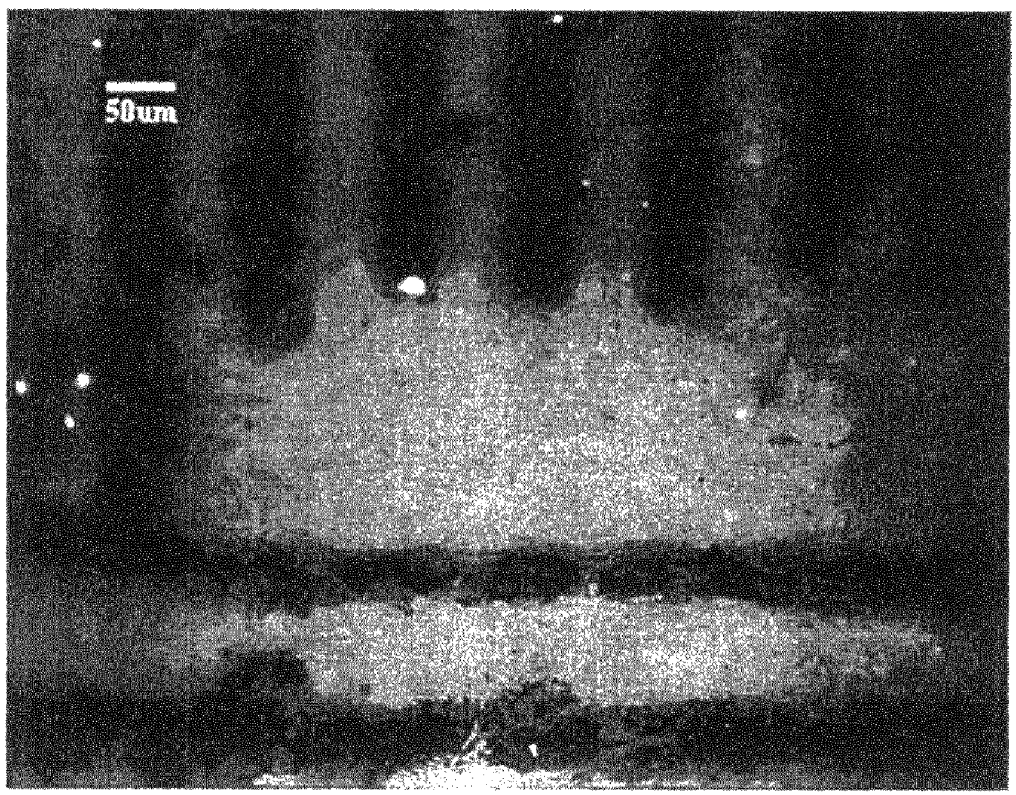
FIG. 7 is a micrograph of the results described in Example XII.

ND particles from the same stock suspension as used in Example I were surface-oxidized and aminated. They were labeled with Alexa Fluor 350 dye (Molecular Probes, Eugene, Oreg,). Those labeled ND particles were delivered to a United States one dollar bill using the Bio-Rad PDS-1000/He system with a 2200 psi rupture disk. The presence of fluorescent particles inside the bill was observed using an Olympus IX71 inverted fluorescence microscope. A micrograph of typical result is shown as FIG. 7. In that micrograph, the scale bar is 50 µm.

EXAMPLE XIII

Figure 8:
FIG. 8 is a micrograph of the results described in Example XIII.

ND particles from the same stock suspension as used in Example I were surface-oxidized and attached to poly-L-lysine-FITC. Those labeled ND particles were delivered to a polyimid film using the Bio-Rad PDS-1000/He system with a 2200 psi rupture disk. Before microscopic observation of the film, the film was thoroughly rinsed with water to assure that fluorescent particles present are within the film. The presence of fluorescent particles inside the film was observed using an Olympus IX71 inverted fluorescence microscope. A micrograph of typical results is shown as FIG. 8. In that micrograph, the scale bar is approximately 50 µm.

EXAMPLE XIV

ND particles from the same stock suspension as used in Example I were surface-oxidized and aminated. They were labeled with Alexa Fluor 350 dye (Molecular Probes, Eugene, Oreg.). Those labeled ND particles were delivered to a polyimid film using the Bio-Rad PDS-1000/He system with an 1100 psi rupture disk. Before microscopic observation of the film, the film was thoroughly rinsed with water to assure that fluorescent particles present are within the film. The presence of fluorescent particles inside the film was observed using an Olympus IX71 inverted fluorescence microscope.

EXAMPLE XV

Figure 13:
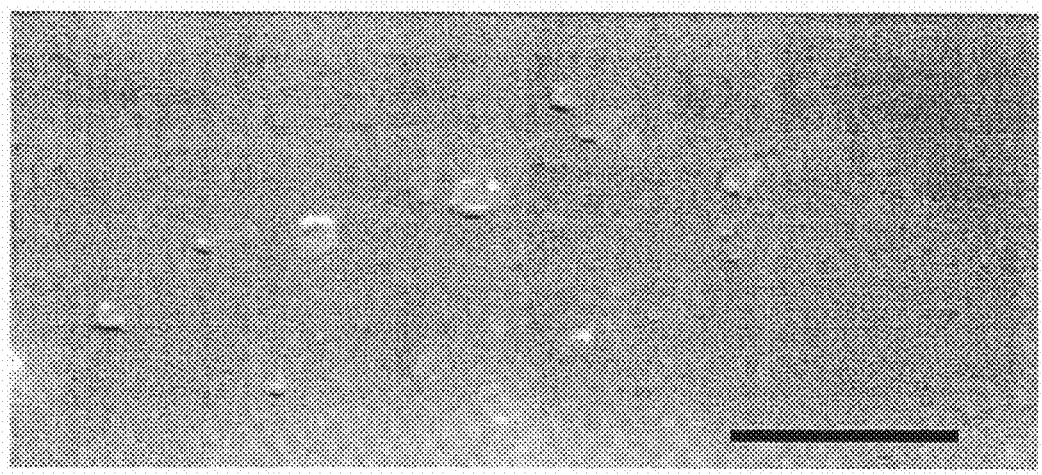
FIG. 13 is a micrograph of the results described in Example XV.

ND particles from the same stock suspension as used in Example I were surface-oxidized. Those labeled ND particles were delivered to the lacquer overcoat of a Sony Supremas™ 700 MB CD-R disc using the Bio-Rad PDS-1000/He system with an 1100 psi rupture disk. Before microscopic observation of the CD-R, the CD-R was thoroughly rinsed with water to assure that ND particles present are within the CD-R. The presence of ND particles inside the CD-R was observed using a Nikon light microscope. A micrograph of typical results is shown as FIG. 13. In that micrograph, the scale bar is 10 µm.

EXAMPLE XVI

Experiments very similar to Example VII were performed in which Multiwall Carbon Nanotubes (MWCNT) were substituted for the ND. The MWCNT used was purchased from Nanostructured and Amorphous Materials, Inc. The MWCNT content in the powder was 95%. The outer diameters were 8-15 nm and the lengths were approximately 500 nm. A total of 80 colonies appeared on the plates. No colonies were observed on the control plates which contained bacteria bombarded with MWCNT without DNA or plates which contained bacteria mixed with plasmid and exposed to a He blast.

EXAMPLE XVII

Figure 14:
FIG. 14 is a micrograph of the results described in Example XVII.

ND particles from the same stock suspension as used in Example I were surface-oxidized and aminated. They were Alexa Fluor labeled. Those labeled ND particles were delivered to a 300 µm thick 001 oriented silicon wafer using the Bio-Rad PDS-1000/He system with an 1100 psi rupture disk. Before microscopic observation of the wafer, the wafer was thoroughly rinsed with water to assure that fluorescent particles present are within the wafer and not merely deposited superficially. The presence of fluorescent particles inside the wafer was observed using an Olympus IX71 inverted fluorescence microscope. A micrograph of typical results is shown as FIG. 14. In that micrograph, the scale bar is approximately 50 µm.

EXAMPLE XVIII

Ethephon is reported to induce ripening. Ethephon, which is not a naturally occurring chemical, is converted by living plant tissue to plant's hormone ethylene. For these experiments, MATURE-AIDE (Chipman, Inc., Ontario, Canada), which contained 40 g/l ethephon, was used. Twenty-five µL of the ND stock used in Example I and 25 µL Mature-aide were mixed, transferred onto a macrocarrier disk and air-dried. The dry mixture was introduced into green mature banana fruit that had not been exposed to ethylene using the Bio-Rad PDS-1000/He system with an 1100 psi rupture disk. Other green mature banana fruit was similarly bombarded with 25 µL of ND particles which were free of MATURE-AIDE. Yet other green mature banana fruit had 25 µL of MATURE-AIDE (without ND particles) spread over a 2-inch spot. Bananas were air ripened at room temperature for 5 days.

Figure 10:
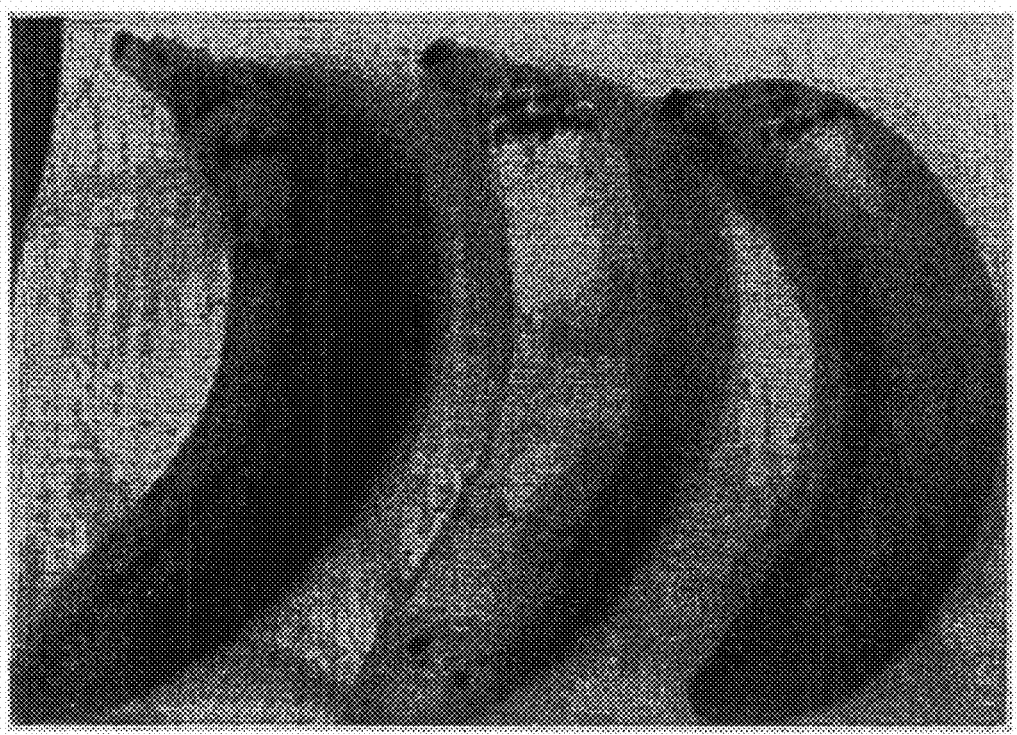
FIG. 10 is a photograph of the results described in Example XVIII.

FIG. 10 is an image of typical results. The banana on the left was fruit which had the MATURE-AIDE (without ND particles) spread over a 2-inch spot. The banana in the middle was bombarded with the ND-MATURE-AIDE mixture. The banana on the right was bombarded with the ND particles (without MATURE-AIDE). Only the middle banana shows considerable ripening and thus no substantial stress ethylene production was induced by the ND bombardment. Enhanced ripening of the middle fruit extended beyond the area bombarded indicating a more general influence on the fruit.

The digit color photograph was digitally manipulated to produce the image in FIG. 10 which is based on the intensity of the red component of the image. The middle banana was predominately yellow and the other bananas were largely green.

EXAMPLE XIX

Diphenylcyclopropenone is a cyclopropene derivative and inhibits ripening. Twenty-five µL of the ND stock described in Example I and 25 µL of 0.05M diphenylcyclopropenone (Acros Organics, Belgium) in ethanol were mixed on the macrocarrier disc and air-dried. The mixture was introduced into green mature banana fruit that had not been exposed to ethylene using the Bio-Rad PDS-1000/He system with an 1100 psi rupture disk. A control banana received no treatment. Bananas were air ripened at room temperature for 10 days.

Figure 11:
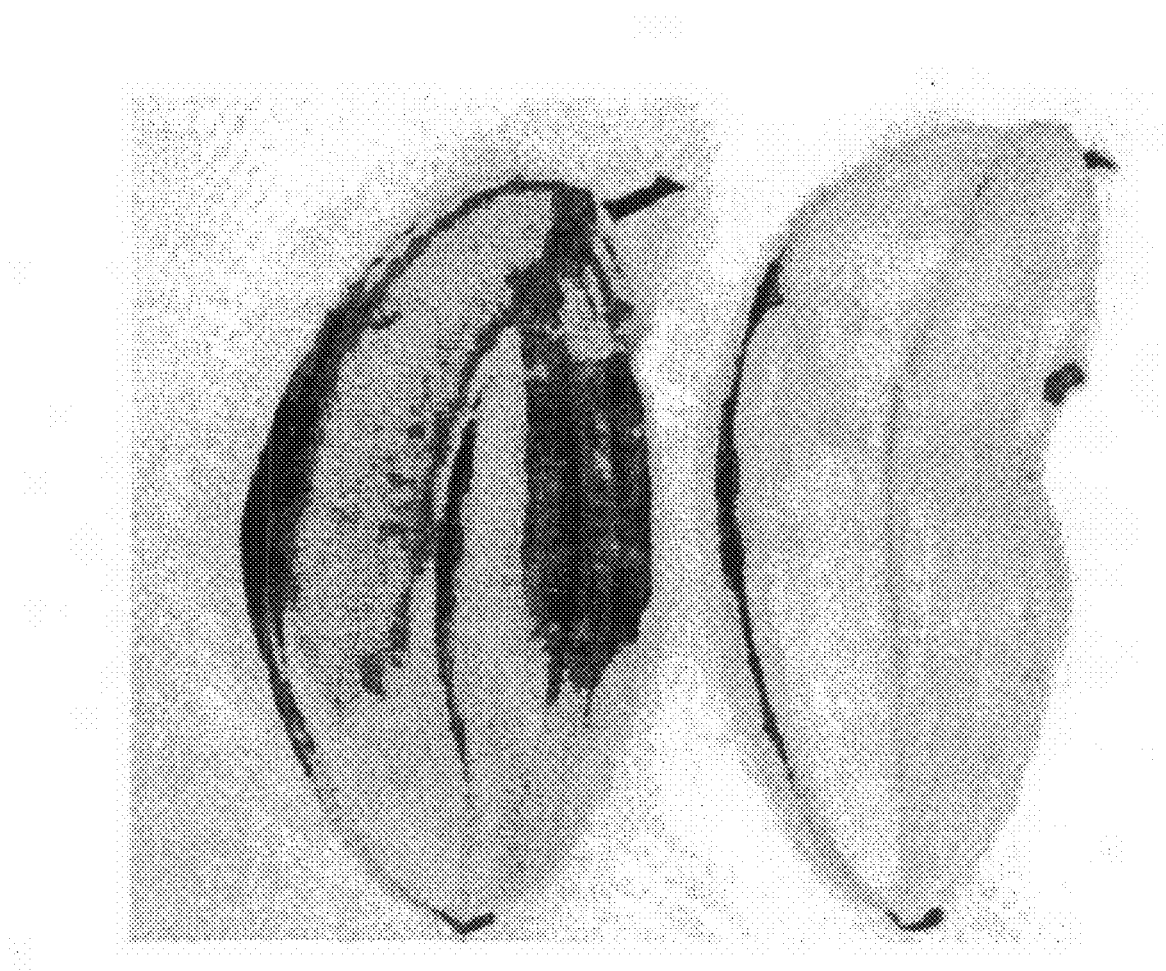
FIG. 11 is a photograph of the results described in Example XIX.

FIG. 11 is a photograph of typical results. The control banana on the left shows considerable ripening. The treated banana on the right shows inhibited ripening. Inhibition of ripening extended beyond the area bombarded indicating a more general influence on the fruit.

EXAMPLE XX

The following PROPHETIC EXAMPLE is provided to illustrate delivery of genetic material to animal cells: For example, based on the experiments reported in this disclosure, it is expected that DNA coding for green fluorescent protein (GFP) could be coated onto ND particles (essentially like the coating of ND particles with plasmid in Example I). Furthermore, based on the experiments reported in this disclosure, it is expected that if a tissue culture monolayer of fall armyworm (*Spodoptera frugiperda*, Sf9, ATCC CRL-1711) was bombarded with those DNA coated ND particles, that some of the cells would express the GFP, which could be observed by fluorescence microscopy.

EXAMPLE XXI

A mixture of ND particles and *E. coli* DH5α in suspension was agitated for 5 minutes on a rotary shaker at 2500 rpm. Then pUC18 was added and the mixture was incubated on ice for 10 minutes. The mixture was plated on LB agar containing 150 µg/ml ampicillin, 0.1 mM IPTG and 60 µg/ml X-gal (Teknova Inc., Hollister, Calif.). Blue colonies were observed on the second day of growth. No blue colonies were observed on the control plates plated with bacteria treated the same except no ND was present during agitation. For this experiment, each blue colony was presumptively founded from a genetically transformed cell.

EXAMPLE XXII

Experiments very similar to Example XVIII were performed in which a 2200 psi rupture disk was used instead of an 1100 psi rupture disk. In those experiments, the results obtained were similar to those obtained with the 1100 psi rupture disk.

EXAMPLE XXIII

Experiments very similar to Example XIX were performed in which a 2200 psi rupture disk was used instead of an 1100 psi rupture disk. In those experiments, the results obtained were similar to those obtained with the 1100 psi rupture disk.

EXAMPLE XXIII

Experiments very similar to Example I were performed in which water was substituted for the Tris-EDTA buffer. Similar results were obtained in those experiments.

EXAMPLE XXIV

Experiments very similar to Example VII were performed in which Single Wall Carbon Nanohorns were substituted for the ND. The Single Wall Carbon Nanohorns were purchased from NanoCraft, Inc. Those nanohorns were 2 to 3 nm in diameter and 30 to 50 nm in length with a 19 degree closed end. They form into clusters with diameters of approximately 30 to 120 nm. A total of 91 colonies appeared on the plates. No colonies were observed on the control plates which contained bacteria bombarded with Single Wall Carbon Nanohorns without DNA or plates which contained bacteria mixed with plasmid and exposed to a He blast.

EXAMPLE XXV

Samples containing ND and OLC were exposed to IR irradiation. Sample of ND used in experiment was obtained from a vendor and was produced by explosion of TNT/RDX in an ice coating and oxidized by ozone treatment of detonation soot. OLC used in the experiment was obtained by annealing of the detonation nanodiamond powder in vacuum ($1*10^{-4}$ torr) as the temperature 1800K for 3 hrs. Three vials with 4 ml of pure water (control sample), 0.7 wt % ND suspension in water (50 nm average particle size) and 0.5 wt % of OLC added to the 0.7 wt % ND suspension (to achieve high sedimentation stability) were prepared. The vial containing OLC suspension was sonicated for 5 min. Thermal couples were inserted into the upper parts of the suspensions and the samples were exposed to a radiation of the Infrared Heat Lamp R40 of Osram Sylvania Products, Inc. Vials were placed at a distance 20 cm from the lamp. The temperature of the suspensions was monitored relatively to the temperature of the control water-containing vial. After exposing the vials to the radiation for 8 min, the temperature increase in the vial with OLC exceeded the temperature increase of the control sample by 18° C. degrees and the vial with the ND particles exceeded the temperature increase of the control sample by 7° C.

EXAMPLE XXVI

Figure 12:
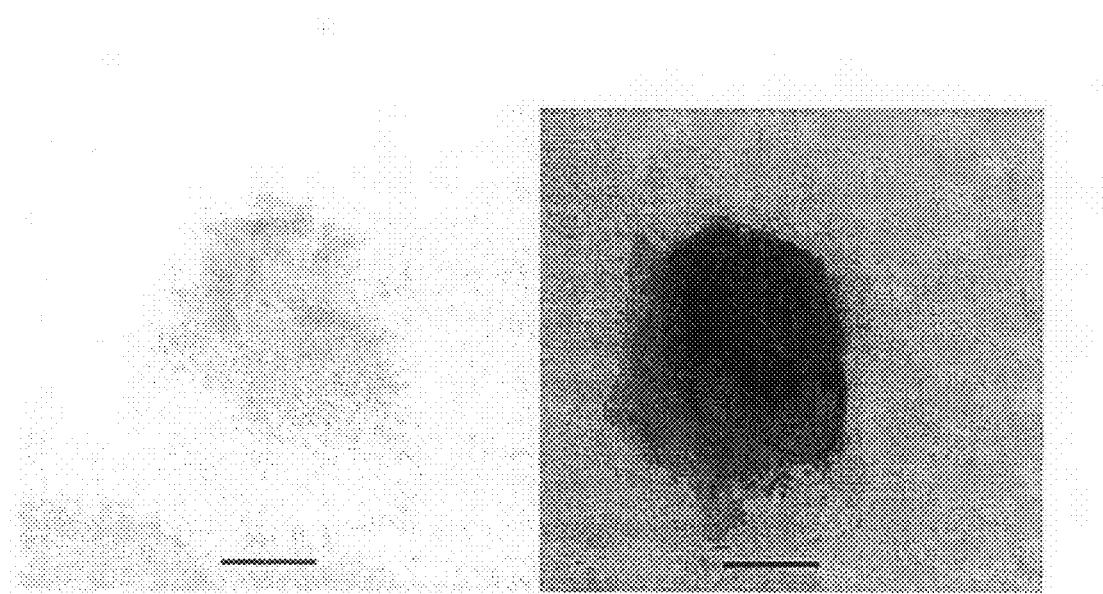
FIG. 12 is a photograph of the results described in Example XXVI.

Sample containing OLC was exposed to IR irradiation OLC particles from the Example XXV were delivered to PARAFILM M® brand thermoplastic laboratory film (Pechiney Plastic Packaging, Inc.) using the Bio-Rad PDS-1000/He system with an 1100 psi rupture disk. A photograph of the resulting sample is illustrated in the left panel of FIG. 12. The sample was exposed at a distance 20 cm in front of the Infrared Heat Lamp R40. In 13 minutes after sample treatment, smoking started in the region containing OLC delivered to the sample. Melted area of the sample in the vicinity of OLC is illustrated in the right panel of FIG. 12. No visible damage was observed for the film area not containing OLC.

EXAMPLE XXVII

Figure 5:
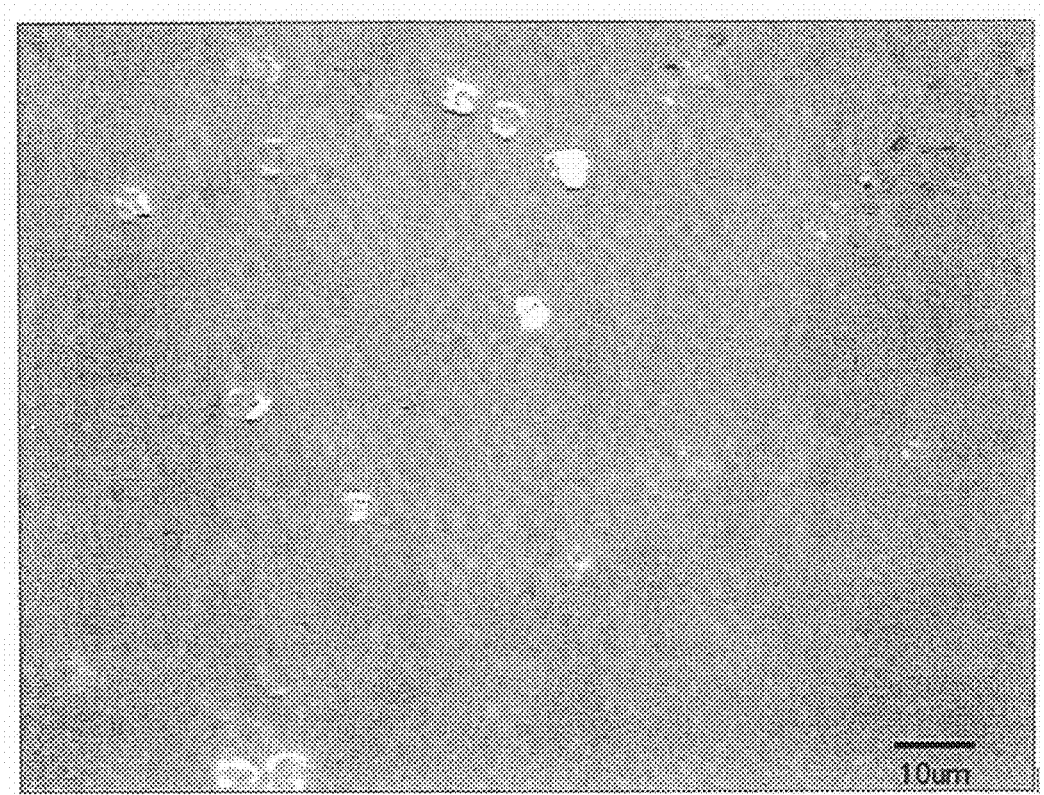
FIG. 5 is a micrograph of the results described in Example XXVII.

ND, obtained from a vendor, had been synthesized by shock wave compression of graphite. The average ND particle (agglomerate) size in water suspension was 400 nm with maximum agglomerate sizes up to several microns. Experiments were performed on samples of 6 ml suspension of 2 wt % of ND with inserted thin film samples to the suspension and sonicated. Sonication was carried out using a sonicator equipped with a tapered titanium horn with a tip diameter 3 mm (COLE-PARMER 750-Watt Ultrasonic Homogenizer EW-04711-60, 20 kHz) that was directly immersed in the sample. The output power was 10 W. The output intensity was approximately 100W/cm$^2$. A 1×1 cm PARAFILM M® film placed in the ND suspension was treated during 5 min. The film was thoroughly rinsed with water and wiped off. FIG. 5 is a micrograph which illustrate significant amount of ND delivered in the presence of sonication to the film.

EXAMPLE XXVIII

Figure 15:
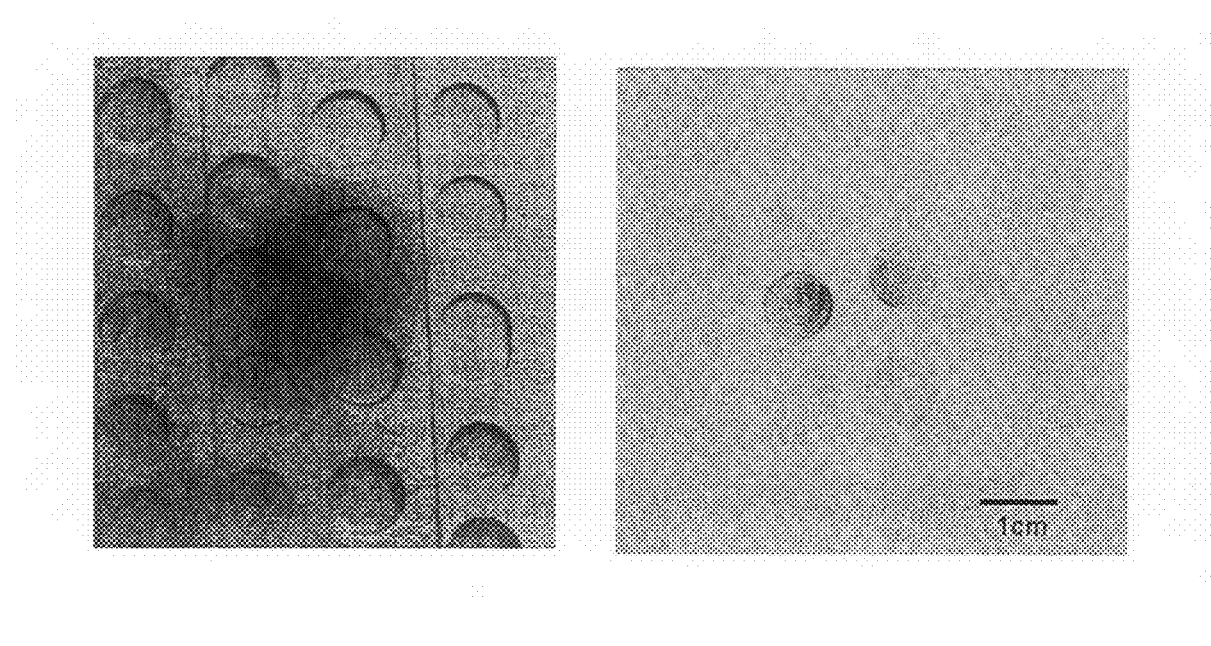
FIG. 15 is a micrograph of the results described in Example XXVIII.

OLC particles from the example XXV were delivered to PARAFILM M® film of Pechiney Plastic Packaging using the Bio-Rad PDS-1000/He system with an 1100 psi rupture disk using a mask to provide a specific pattern of the delivered particles in the target. A mask was composed of circular 5 mm in diameter openings in a gloss sticker paper attached to the PARAFILM M® film during OLC delivery. The PARAFILM M® film with mask are shown after particle delivery in the left panel of FIG. 15. After bombardment OLC was delivered to the place corresponding to the opened area of the mask. Photograph of the resulting sample (after the mask was removed) is illustrated in the right panel of FIG. 15.

EXAMPLE XXIX

OLC was dispersed in Banana Boat tanning lotion SPF 4 formulation (1 wt %), 0.2 g of the formulation was placed between two polyethylene films. Similar control sample was prepared without OLC. The samples were placed at a distance 20 cm from the Infrared Heat Lamp R40. In 5 minutes after beginning of radiation high temperature increase in the sample containing OLC resulted in polyethylene films melting and bonding together while the control sample didn't melt.

EXAMPLE XXX

Figure 9:
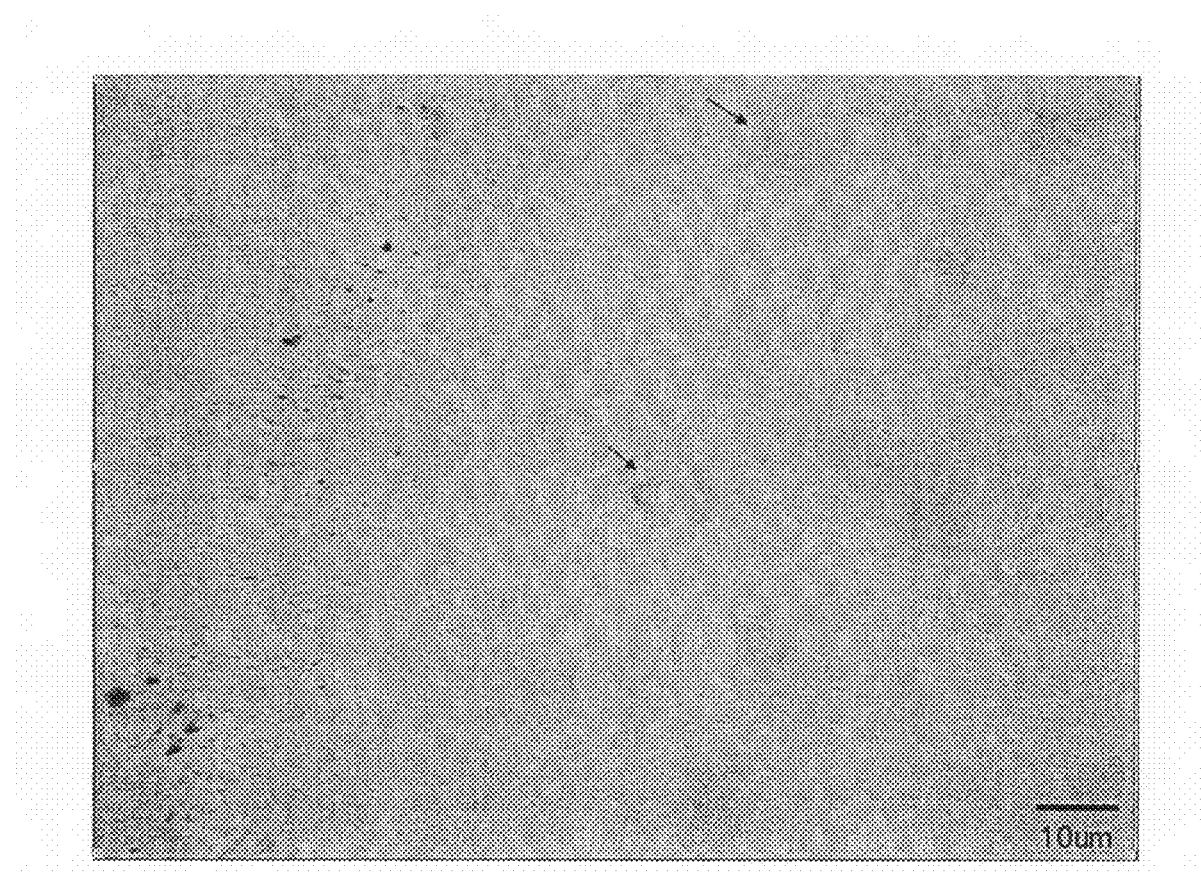
FIG. 9 is a micrograph of the results described in Example XXX.

This example is simple to Example XXVII except that gold foil was used instead of PARAFILM M® film. FIG. 9 is a micrograph which shows ND delivered in the presence of sonication to the film (indicated by arrows). The number of particles delivered was lower than in Example XXVII.

This disclosure included examples of diverse substances being delivered to diverse targets. Embodiments of the invention disclosed here could be used to deliver a wide range of substances, including those used in the disclosed examples and those substances not used in the disclosed examples. The "substances" introduced may, for example, potentially be from many classes of substances including, but not limited to, markers, nucleic acids, dyes, proteins, biologically active substances, biologically inactive substances, elements, compositions, drugs, enzymes, and mixtures of such substances. These examples are presented by way of illustration, and the invention should not be construed to be limited to such examples or the examples used in the experiments described herein. Moreover, all of the illustrated substances may not prove useful for delivery to all potential targets.

It is specifically envisioned that the embodiments of the invention disclosed here could involve the employment of more than one kind of nanoparticle. Those embodiments would include both cases in which more than one type of nanocarbon particle was employed and cases in which nanocarbon particles and other nanoparticles are employed. Ballistic delivery of DNA-coated nanodiamonds has a potential to become an advanced method for delivering DNA in the intact prokaryotic and eukaryotic cells both in vivo and in vitro and to deliver proteins, drugs and other substances.

Some of the embodiments of the invention disclosed here involve using ND particles as biolistic delivery-aids. Advantages of ND as biolistic delivery-aids can include, it least in some circumstances the following. Diamond is known to be a highly biologically compatible material. ND particles are rigid, mechanically stable, has inert core and can be made of any desirable size. ND particle are less expensive than commercially available particles made of, for example, gold. This could be especially beneficial in application such as, vaccination of animals or plants transformation which would be prohibitively costly using gold carriers. ND particles can be sterilized by exposure to a high temperature and stored for a long time without oxidation. ND particles can be functionalized with a wider variety of surface groups that can be linked to different biosubstances than currently used gold particles can. ND particles coated with bio-compounds can be stored for long period of time. It is important to note that there are uses of the invention disclosed here that have few or none of the advantages stated in this paragraph. It is also noted that failure of any particular embodiment to have any or all of the features or advantages described herein does not preclude the embodiment from falling within the scope of the present invention.

Based on certain examples disclosed, it is apparent that in accordance with certain embodiments, a delivery method can be used to deliver nanoparticles, alone or in combination with a substance that uses the nanoparticles as a delivery aid, to a particular region of the target. In certain embodiments, the region of the target may be defined by a mask situated between the source of particles and the target. In accordance with certain embodiments, subsequent irradiation of the target can be used to induce localized heating in the region of the target in which the particles are delivered according to certain embodiments. In certain other embodiments, it is envisioned that a mask can be used to create a pattern of the nanoparticles in the target, for example without limitation, as a mechanism for labeling or tagging the target. By way of example, and not limitation, this could be used for purposes of later identification or tracing of a particular target. Other applications will occur to those skilled in the art upon consideration of the present teachings.

It is specifically contemplated that ballistic delivery could be accomplished by means of accelerating the particles other than the specific means used in the examples above. As one of many possibilities, the particles could be accelerated by a chemical explosion (e.g., gunpowder) rather than by the explosive release of an inert gas. Acceleration of particles could be incident to electrically pulsed atmospheric pressure plasma formation.

It should be understood that the targets used in the examples should be viewed as mere illustrations. It is apparent from the wide variety of materials, living and non-living, used as targets, that the methods disclosed here are quite general in terms of the possible targets. In the case of living targets, it is specifically envisioned that the variety of living things that could be targets is quite wide. It is also specifically envisioned that those cells may be found in culture, in a whole organism or in tissues. It is also specifically envisioned that the delivery may be to living things, or structures that include metabolically active cells, in which all or some of the substance delivered does not enter cells within the target. This could include the substance, once delivered, being dispersed. That dispersion may be by simple diffusion, net flow of fluids or by other means. That dispersion could happen, to state a few examples, within a fruit, within an animal organ or widely through an animal blood stream.

It should be understood that the substances introduced to targets in the examples should be viewed as mere illustrations. It is apparent from the wide variety of substances introduced to targets that the methods disclosed here are quite general in terms of possible substances to be introduced to targets.

Thus, in accordance with certain embodiments consistent with the present invention, method of delivering a substance to a target involves delivery of said substance with a delivery-aid which comprises nanocarbon particles. In certain embodiments, the target may be living cells such as prokaryotic cells, animal cells, fungal cells, or plant cells. In other embodiments, the target may be interstitial materials. The target may also be metabolically active cells in certain structures. The substance delivered may be, for example, nucleic acid, a dye, or a biologically active substance or combination thereof. The target may also be non-living solid such as a polymer, composite, metal or a semiconductor. The target could also be a non-living material which is not solid. The delivery-aid may be nanodiamonds, onion-like carbon particles, multiwall carbon nanotubes or single wall carbon nanohorns or combination thereof. The delivery may be ballistic or non-ballistic. The substance may be attached to the nanocarbon by chemical bonds or deposited onto the nanocarbon. Other embodiments will occur to those skilled in the art upon consideration of the present teachings.

In accordance with certain embodiments, a method of genetically transforming living cells involve the following steps, in any order, or at least partially, concurrently, exposing the cells to nanocarbon and exposing the cells to genetic material. In one embodiment, the cells are agitated in the presence of nanocarbon. The cells, for example, may be prokaryotic cells. Other embodiments will occur to those skilled in the art upon consideration of the present teachings.

In accordance with certain embodiments, a method of rendering cells competent involves exposing those cells to nanocarbon particles. The nanocarbon may be, for example, nanodiamonds, single wall carbon nanohorns, carbon onions, onion-like carbon particles or carbon nanotubes. The living cells may be prokaryotic cells. Other embodiments will occur to those skilled in the art upon consideration of the present teachings.

From the above description and drawings, it will be understood by those of ordinary skill in the art after consideration of the present teachings that the particular embodiments shown and described are for purpose of illustration only, and are not intended to limit the scope of the invention. Those of ordinary skill in the art will recognize, after consideration of the present teachings, that the invention may be embodied in other specific forms without departing from its spirit or essential characteristics. References to details of particular embodiments are not intended to limit the scope of the claims.

No claim element herein is to be construed under the provisions of 35 U.S.C. §112, sixth paragraph, unless the element is expressly recited using the phrase "means for" or "step for."

The invention claimed is:

1. A method of genetically transforming living cells comprising the concurrent steps of exposing the cells to nanoparticles and exposing the cells to genetic material, wherein the living cells comprise animal cells and the nanoparticles comprise nanodiamond particles.

2. A method according to claim 1 in which cells and nanoparticles are agitated in the presence of each other.

3. A genetically transformed living animal cell, transformed according to the method of claim 1.

4. A method of delivering a substance to a target comprising delivery of said substance with a delivery-aid which comprises nanocarbon particles to said target, wherein said target comprises living animal cells, said delivery-aid comprises at least one nanodiamond and at least one nucleic acid, and said delivery comprises ballistic delivery.

5. The method of claim 4, wherein delivery of said delivery aid genetically transforms at least one of said living cells.

6. The method of claim 4, in which said nucleic acid is covalently attached to the nanodiamond.

7. The method of claim 6, in which said nanodiamond is functionalized.

8. The method of claim 7, in which said nanodiamond is aminated.

9. The method of claim 4, in which said nucleic acid is non-covalently attached to the nanodiamond.

10. The method of claim 4, wherein said delivery aid comprises a drug.

11. The method of claim 4, wherein said delivery aid comprises a marker, dye, protein, biologically active substance, biologically inactive substance, element, drug, enzyme, or combination thereof.

12. A method of delivering a substance to a target comprising delivery of a substance with a delivery-aid which comprises nanocarbon particles to said target, wherein said target comprises living animal cells, said delivery-aid comprises nanodiamonds, and said substance comprises a nucleic acid.

13. The method of claim 12, in which said nucleic acid is covalently attached to the nanodiamond.

14. The method of claim 13, in which said nanodiamond is functionalized.

15. The method of claim 14, in which said nanodiamond is aminated.

16. The method of claim 12, in which said nucleic acid is non-covalently attached to the nanodiamond.

17. The method of claim 12, wherein said delivery aid comprises a drug.

18. The method of claim 12, wherein said delivery aid comprises a marker dye, protein, biologically active substance, biologically inactive substance, element, drug, enzyme, or combination thereof.

* * * * *